United States Patent [19]
Sato et al.

[11] Patent Number: 5,206,421
[45] Date of Patent: Apr. 27, 1993

[54] METHOD FOR PRODUCING 4-HYDROXYBUTYL (METH)ACRYLATE

[75] Inventors: Toshihiro Sato; Masao Kobayashi, both of Otake, Japan

[73] Assignee: Mitsubishi Rayon Co., Ltd., Tokyo, Japan

[21] Appl. No.: 715,244

[22] Filed: Jun. 14, 1991

[30] Foreign Application Priority Data

Jul. 11, 1990 [JP] Japan .................................. 2-181484

[51] Int. Cl.$^5$ ....................... C07C 69/52; C07C 67/05
[52] U.S. Cl. ..................................... 560/224; 560/205
[58] Field of Search ............................... 560/224, 205

[56] References Cited

FOREIGN PATENT DOCUMENTS 1518572  1/1969  Fed. Rep. of Germany ...... 560/205
7213905 10/1972  Fed. Rep. of Germany ...... 560/205

Primary Examiner—José G. Dees
Assistant Examiner—Keith MacMillan
Attorney, Agent, or Firm—Armstrong, Westerman, Hattori, McLeland & Naughton

[57] ABSTRACT

4-Hydroxybutyl (meth)acrylate is prepared by reacting (meth)acrylic acid with 1,4-butanediol in the presence of an acidic catalyst. 1,4-Butanediol di(meth)acrylate is added at the beginning of the reaction and the ratios of the butanediol to the acid and of the ester to the acid are kept within specified ranges during the course of the reaction.

2 Claims, No Drawings

METHOD FOR PRODUCING 4-HYDROXYBUTYL (METH)ACRYLATE

BACKGROUND OF THE INVENTION

1. Field of the Invention

The present invention relates to a method for producing 4-hydroxybutyl (meth)acrylate which is a monomer suitable for producing paint vehicles used to improve the adhesion property and weather resistance of paints by polymerization thereof.

2. Description of the Prior Art

Generally, when acrylic acid or methacrylic acid is reacted with a diol represented by the formula (1) in the presence of an acidic catalyst, hydroxyalkyl mono(meth)acrylate represented by the formula (2) is obtained, $$HO(CH_2)_nOH \quad (n>2) \quad (1)$$

$$CH_2=CRCOO(CH_2)_nOH \quad (n>2) \quad (2)$$

wherein R represents a hydrogen atom or a methyl group.

In this synthetic reaction, however, alkylene glycol di(meth)acrylate represented by the formula (3) is produced as a by-product at the same time with the desired hydroxyalkyl mono(meth)acrylate, $$CH_2=CRCOO(CH_2)_nOCOCR=CH_2 \quad (n>2) \quad (3)$$

In this case, formation of the di(meth)acrylate, a by-product, can fairly be inhibited if the molar ratio of a diol to (meth)acrylic acid at the time of feeding is made very large. However, complete inhibition of formation of the di(meth)acrylate, a by-product, is impossible even by such a means. This formation is due to that the reactivity of hydroxyl groups of the diol is substantially equivalent to that of the hydroxyl group of the mono(meth)acrylate, so that formation of the di(meth)acrylate as a by-product is difficult to avoid. Further, there are defects that when the molar ratio of a diol to acrylic or methacrylic acid at the time of feeding is made large, the diol present in a large amount in the reaction system after the completion of the reaction must be separated from hydroxyalkyl mono(meth)acrylate in good efficiency, and besides that the productivity is low because of the diol being used in large amounts.

Also, 4-hydroxybutyl (meth)acrylate and 1,4-butanediol di(meth)acrylate are compounds having boiling points of 230° C. and 275° C., respectively, and being very easily polymerizable and rich in reactivity, so that separation of the both by distillation is almost impossible.

In order to solve these problems, a method is disclosed in which in the continuous production of the monohydroxy ester of a diol by the reaction of the diol with an organic acid in the presence of an acid catalyst, the diester produced as a by-product is separated from the reaction product and returned to the reaction system (DE 1518572 A1). This method converts the diester, a by-product, into the monoester by solvolysis, so that a rise in the yield based on the organic acid can be expected. However the yield based on the diol is so low that an improvement is necessary to use the above method in industry.

SUMMARY OF THE INVENTION

In a method for producing 4-hydroxybutyl (meth)acrylate by reacting (meth)acrylic acid with 1,4-butanediol in the presence of an acidic catalyst, the present invention relates to the improvement in which 1,4-butanediol di(meth)acrylate is added from the beginning of the reaction so that a relationship represented by the equation (I), $$1 > \frac{[\text{number of moles of 1,4-butanediol}]}{[\text{number of moles of (meth)acrylic acid}]} > 0.5 \quad (I)$$

is maintained in the reaction system, and besides the molar ratio of added 1,4-butanediol di(meth)acrylate to added (meth)acrylic acid is in a range represented by the equation (II), $$1.3 > \frac{[\text{number of moles of 1,4-butanediol di(meth)acrylate}]}{[\text{number of moles of (meth)acrylic acid}]} > 0.7 \quad (II)$$

provided that in calculating the equation (I), both the 1,4-butanediol di(meth)acrylate and 4-hydroxybutyl (meth)acrylate which are present in the reaction system by addition at the beginning of the reaction or formation during the reaction are included in the calculation by taking 1,4-butanediol di(meth)acrylate to correspond to the presence of 1 mole of 1,4-butanediol and 2 moles of (meth)acrylic acid per 1 mole thereof, an 4-hydroxybutyl (meth)acrylate to correspond to the presence of 1 mole of 1,4-butanediol and 1 mole of (meth)acrylic acid per 1 mole thereof.

DESCRIPTION OF THE PREFERRED EMBODIMENTS

The present invention is one based on the novel idea that in the reaction of (meth)acrylic acid with 1,4-butanediol in which formation of 1,4-butanediol di(meth)acrylate, a by-product, is not avoidable, the amount of 1,4-butanediol di(meth)acrylate thought to be newly formed as a by-product by the reaction is reduced by causing 1,4-butanediol di(meth)acrylate to exist in the reaction system from the beginning of the reaction. When acrylic acid is used in the reaction, 1,4-butanediol diacrylate is added, and when methacrylic acid is used in the reaction, 1,4-butanediol dimethacrylate is added.

The molar ratio of (meth)acrylic acid, 1,4-butanediol and 1,4-butanediol di(meth)acrylate to be fed at the beginning of the reaction needs to be strictly determined as described above so that the yields take the most preferred values based on both (meth)acrylic acid and 1,4-butanediol.

When the reaction is carried out under the condition that the value of the above equation (I) is not less than 1 or not more than 0.5, reduction in the yields based on both (meth)acrylic acid and 1,4-butanediol is too large to be practical. The value of the equation (I) is preferably in a range of 0.6 to 0.9.

As a catalyst for the esterification, commonly used acidic catalysts such as sulfonic acids, sulfuric acid, acidic ion-exchange resins, etc. can be used.

In carrying out the reaction, an inert azeotropic solvent which forms an azeotropic mixture with water during the reaction may be caused to exist in the reaction system. The ageotropic mixture separates into the solvent and water when it condenses and is allowed to stand. Such the solvent includes for example pentane, hexane, heptane, benzene, toluene, etc. Usually, the azeotropic solvent is used in a range of 0.1 to 0.8 part by weight based on the reaction solution.

Water produced by the reaction forms an azeotropic mixture with the inert azeotropic solvent and is distilled out of the system at a distillation column installed on the top of the reactor. Since this azeotropic mixture condenses to separate into an aqueous phase and a solvent phase, the reaction is caused to proceed while removing the aqueous phase out of the system and returning the solvent phase to the reactor. The reaction has come to an end at a point when the outward flow of water is no longer observed.

The reaction time is usually from 5 to 25 hours.

The reaction temperature is determined by the refluxing temperature, but particularly, a range of 60° to 100° C. is preferred in terms of the inhibition of polymerization and quality of products.

As a polymerization inhibitor, hydroquinone, hydroquinone monomethyl ether, phenothiazine, etc. are used. The reaction is carried out, preferably while supplying air, after adding the polymerization inhibitor so that its concentration is 100 to 1000 ppm.

The reaction may be carried out in a batch operation or a continuous operation.

After completion of the reaction, the catalyst is removed if necessary from the reaction solution which is then washed with an alkali and then with water. If the azeotropic solvent used in the reaction is different from an extraction solvent used in after-treatment, the former is first distilled off. Then, the extraction solvent is added to extract 1,4-butanediol di(meth)acrylate.

As the extraction solvent used in the present invention, it is desirable to use one or more solvents selected from the group consisting of pentane, cyclopentane, hexane, cyclohexane, heptane, cycloheptane, octane and branched alkanes having 5 to 8 carbon atoms.

Usually, the amount of the extraction solvent used is preferably in a range of 0.5 to 10 parts by weight based on a mixture containing 4-hydroxybutyl (meth)acrylate and 1,4-butanediol di(meth)acrylate.

On leaving still after mixing the extraction solvent and the reaction solution, the mixture separates into two phases, and 1,4-butanediol di(meth)acrylate selectively passes into the separated extraction solvent phase. In this case, 4-hydroxybutyl (meth)acrylate, a desired compound, can be obtained in higher yields by washing the extraction solvent phase with a suitable amount of water of recover a small amount of 4-hydroxybutyl (meth)acrylate dissolved in the extraction solvent phase into a washing, and then adding the washing to the other phase mainly containing 4-hydroxybutyl (meth)acrylate of the above two phases.

This extraction operation may be carried out repeatedly or in any of batch operation and continuous operation.

On removing the extraction solvent from the extraction solvent phase by distillation, a solution containing 1,4-butanediol di(meth)acrylate as a main component remains behind. This solution may be re-used by returning to the reaction system.

On the other hand, since the other phase described above contains, in addition to the desired 4-hydroxybutyl (meth)acrylate which is a main component, small amounts of water, the extraction solvent, etc., it can be purified by removing low-boiling components and subjecting to distillation as need arises.

The present invention will be illustrated in more detail with reference to the following examples, but it is not to be interpreted as being limited thereto.

EXAMPLE 1

To a reactor equipped with a reflux condenser, a thermometer and a stirrer were added 720 g (10 moles) of acrylic acid, 1022 g (11.35 moles) of 1,4-butanediol and 2155 g (10.88 moles) of 1,4-buatnediol diacrylate, after which 1.5 g of hydroquinone (polymerization inhibitor), 60 g of p-toluenesulfonic acid (catalyst) and 925 g of n-hexane (azeotropic solvent) were added.

In this case, the value of the equation, $$\frac{[\text{number of moles of 1,4-butanediol}]}{[\text{number of moles of acrylic acid}]}, \text{ was } 0.7,$$

provided that in calculating this equation, both 1,4-butanediol diacrylate and 4-hydroxybutyl acrylate present in the reaction system were included in the calculation by taking the former diacrylate to correspond to the presence of 1 mole of 1,4-butanediol and 2 moles of acrylic acid per 1 mole thereof and the latter acrylate to correspond to the presence of 1 mole of 1,4-butanediol and 1 mole of acrylic acid per 1 mole thereof. Further, the molar ratio of added 1,4-butanediol diacrylate to acrylic acid added for reaction with 1,4-butanediol, represented by the equation, $$\frac{[\text{number of moles of 1,4-butanediol diacrylate}]}{[\text{number of moles of acrylic acid}]}, \text{ was } 1.09.$$

The reaction was carried out at a temperature of 70° to 80° C. while azeotropically removing water produced by the reaction together with n-hexane, and continued until the water ceased to flow out. The reaction solution was cooled and analyzed.

As a result, it was found that the conversion of acrylic acid was 99.5%, that of 1,4-butanediol was 94.0% and the selectivity of 4-hydroxybutyl acrylate was 99.0% and 92.3% based on acrylic acid and 1,4-butanediol, respectively.

The conversion and selectivity were calculated according to the following equations:

$$[\text{Conversion of acrylic acid}] = \frac{[\text{number of moles of reacted acrylic acid}]}{[\text{number of moles of fed acrylic acid}]} \times 100\ (\%)$$

$$[\text{Conversion of 1,4-butanediol}] = \frac{[\text{number of moles of reacted 1,4-butanediol}]}{[\text{number of moles of fed 1,4-butanediol}]} \times 100\ (\%)$$

$$[\text{Selectivity of 4-hydroxybutyl acrylate (based on acrylic acid)}] = \frac{[\text{number of moles of produced 4-hydroxybutyl acrylate}]}{[\text{number of moles of reacted acrylic acid}]} \times 100\ (\%)$$

$$[\text{Selectivity of 4-hydroxybutyl acrylate (based on 1,4-butanediol)}] = \frac{[\text{number of moles of produced 4-hydroxybutyl acrylate}]}{[\text{number of moles of reacted 1,4-butanediol}]} \times 100\ (\%)$$

COMPARATIVE EXAMPLE 1

Reaction was carried out in the same manner as in Example 1 except that 1,4-butanediol diacrylate was not added. In this case, the value of the equation, $$\frac{[\text{number of moles of 1,4-butanediol}]}{[\text{number of moles of acrylic acid}]}, \text{ was } 1.14.$$

As a result, it was found that the conversion of acrylic acid was 99.5%, that of 1,4-butanediol was 94.0% and the selectivity of 4-hydroxybutyl acrylate was 73.0% and 68.0% based on acrylic acid and 1,4-buatanediol, respectively.

The conversion and selectivity were calculated according to the equations described in Example 1.

COMPARATIVE EXAMPLE 2

Reaction was carried out in the same manner as in Comparative Example 1 except that the amount of 1,4-butanediol fed was 630 g. In this case, the value of the equation, $$\frac{[\text{number of moles of 1,4-butanediol}]}{[\text{number of moles of acrylic acid}]}$$

was 0.7.

As a result, it was found that the conversion of acrylic acid was 98.3%, that of 1,4-butanediol was 94.4% and the selectivity of 4-hydroxybutyl acrylate was 30.1% and 44.8% based on acrylic acid and 1,4-butanediol, respectively.

The conversion and selectivity were calculated according to the equations described in Example 1.

COMPARATIVE EXAMPLE 3

Procedure was repeated in the same manner as in Example 1 except that the amount of 1,4-butanediol added was 307 g (3.41 moles). In this case, the following values were obtained on the molar ratio (a) of the materials added and the molar ratio (b) of the compounds present in the reaction system:

$$\frac{[\text{number of moles of 1,4-butanediol diacrylate}]}{[\text{number of moles of acrylic acid}]} = 1.09 \quad (a)$$

$$\frac{[\text{number of moles of 1,4-butanediol}]}{[\text{number of moles of acrylic acid}]} = 0.45 \quad (b)$$

In calculating the equation (b), 1,4-butanediol diacrylate present in the reaction system was taken to correspond to the presence of 1 mole of 1,4-butanediol and 2 moles of acrylic acid per 1 mole thereof, and 4-hydroxybutyl acrylate present in the reaction system was taken to correspond to the presence of 1 mole of 1,4-butanediol and 1 mole of acrylic acid per 1 mole thereof.

The conversion of acrylic acid was 64.5%, and the selectivity of 4-hydroxybutyl acrylate based on acrylic acid was 0.5%.

The conversion of 1,4-butanediol was 99.0%, and the selectivity of 4-hydroxybutyl acrylate based on 1,4-butanediol was 1.0%.

COMPARATIVE EXAMPLE 4

Procedure was repeated in the same manner as in Example 1 except that the amount of 1,4-butanediol added was 2280 g (25.3 moles). In this case, the following values were obtained on the molar ratio (a) of the materials added and the molar ratio (b) of the compounds present in the reaction system:

$$\frac{[\text{number of moles of 1,4-butanediol diacrylate}]}{[\text{number of moles of acrylic acid}]} = 1.09 \quad (a)$$

$$\frac{[\text{number of moles of 1,4-butanediol}]}{[\text{number of moles of acrylic acid}]} = 1.14 \quad (b)$$

In calculating the equation (b), 1,4-butanediol diacrylate present in the reaction system was taken to correspond to the presence of 1 mole of 1,4-butanediol and 2 moles of acrylic acid per 1 mole thereof, and 4-hydroxybutyl acrylate present in the reaction system was taken to correspond to the presence of 1 mole of 1,4-butanediol and 1 mole of acrylic acid per 1 mole thereof.

The conversion of acrylic acid was 98.4%, and the selectivity of 4-hydroxybutyl acrylate based on acrylic acid was 98.0%.

The conversion of 1,4-butanediol was 70.0%, and the selectivity of 4-hydroxybutyl acrylate based on 1,4-butanediol was 93.3%.

As shown above, when the reaction was carried out under the condition that the number of moles of 1,4-butanediol present in the reaction system was larger than that of acrylic acid present in the reaction system, a large quantity of 1,4-butanediol remained unreacted after completion of the reaction, so that separation of 1,4-butanediol from 4-hydroxybutyl acrylate became difficult in the subsequent purification step.

EXAMPLE 2

Reaction was carried out according to Example 1. The reaction solution, after neutralized, was continuously supplied to the 33rd stage of a 40-stage agitated compartmented extractor of 50 mm in diameter at a rate of 580 g/hr. Similarly, n-hexane was continuously supplied to the 1st stage of the extractor at a rate of 2000 g/hr, and water was continuously supplied to the 40th stage of the extractor at a rate of 60 g/hr. n-Hexane was recovered from the liquid flowing out of the uppermost part of the extractor to obtain 2250 g of 1,4-butanediol diacrylate. From the liquid withdrawn from the bottom of the extractor was removed low-boiling components under reduced pressure, and then the residual liquid was subjected to thin-film distillation under reduced pressure to obtain 1350 g of 4-hydroxybutyl acrylate. This amount corresponds to yields of 93.6% and 82.6% based on acrylic acid and 1,4-butanediol fed, respectively.

EXAMPLE 3

Reaction, recovery and purification were carried out in the same manner as in Example 2 except that cyclohexane was used in place of n-hexane to confirm that almost the same result as in Example 1 was obtained.

EXAMPLE 4

Reaction, recovery and purification were carried out in the same manner as in Example 2 except that n-heptane was used in place of n-hexane to confirm that almost the same result as in Example 1 was obtained.

EXAMPLE 5

To a reactor equipped with a reflux condenser, a thermometer and a stirrer were added 860 g of methacrylic acid, 900 g of 1,4-butanediol and 2260 g of 1,4-butanediol dimethacrylate, after which 1.5 g of hydroquinone (polymerization inhibitor), 60 g of p-toluenesulfonic acid (catalyst) and 1000 g of n-hexane (azeotropic solvent) were added.

In this case, the value of the equation, $$\frac{[\text{number of moles of 1,4-butanediol}]}{[\text{number of moles of methacrylic acid}]}, \text{ was } 0.7,$$

provided that in calculating this equation, both 1,4-butanediol dimethacrylate and 4-hydroxybutyl methacrylate present in the reaction system were included in the calculation by taking the former dimethacrylate to correspond to the presence of 1 mole of 1,4-butanediol and 2 moles of methacrylic acid per 1 mole thereof and the latter methacrylate to correspond to the presence of 1 mole of 1,4-butanediol and 1 mole of methacrylic acid per 1 mole thereof. Further, the molar ratio of added 1,4-butanediol dimethacrylate to methacrylic acid added for reaction with 1,4-butanediol, represented by the equation, $$\frac{[\text{number of moles of 1,4-butanediol dimethacrylate}]}{[\text{number of moles of methacrylic acid}]},$$

was 1.0.

The reaction was carried out at a temperature of 70° to 85° C. while azeotropically removing water produced by the reaction together with n-hexane, and continued until the water ceased to flow out. The reaction solution was cooled and analyzed.

As a result, it was found that the conversion of methacrylic acid was 99.1%, that of 1,4-butanediol was 94.0% and the selectivity of 4-hydroxybutyl methacrylate was 99.0% and 93.0% based on methacrylic acid and 1,4-butanediol, respectively.

The conversion and selectivity were calculated according to Example 1.

What is claimed is:

1. In a method for producing 4-hydroxybutyl (meth)acrylate by reacting (meth)acrylic acid with 1,4-butanediol in the presence of an acidic catalyst, the improvement in which 1,4-butanediol di(meth)acrylate is added from the beginning of the reaction so that a relationship represented by the following equation, $$1 > \frac{[\text{number of moles of 1,4-butanediol}]}{[\text{number of moles of (meth)acrylic acid}]} > 0.5 < 1$$

is maintained in the reaction system, and besides the molar ratio of added 1,4-butanediol di(meth)acrylate to added (meth)acrylic acid is in a range represented by the following equation, $$1.3 > \frac{[\text{number of moles of 1,4-butanediol di(meth)acrylate}]}{[\text{number of moles of (meth)acrylic acid}]} > 0.7$$

provided that in calculating the former equation, both the 1,4-butanediol di(meth)acrylate and 4-hydroxybutyl (meth)acrylate which are present in the reaction system by addition at the beginning of the reaction or formation during the reaction are included in the calculation by taking 1,4-butanediol di(meth)acrylate to correspond to the presence of 1 mole of 1,4-butanediol and 2 moles of (meth)acrylic acid per 1 mole thereof, and 4-hydroxybutyl (meth)acrylate to correspond to the presence of 1 mole of 1,4-butanediol and 1 mole of (meth)acrylic acid per 1 mole thereof.

2. A method according to claim 1, wherein after completion of the reaction, 1,4-butanediol di(meth)acrylate is extracted from the reaction solution using, as an extraction solvent, at least one selected from the group consisting of pentane, hexane, heptane and octane to obtain an extract containing 1,4-butanediol di(meth)acrylate, 4-hydroxybutyl (meth)acrylate is recovered from the residual solution after extraction, and said extract containing 1,4-butanediol di(meth)acrylate, as it is or after removing the extraction solvent therefrom, is returned again to the reaction system.

* * * * *